United States Patent [19]
Stig et al.

[11] Patent Number: 5,464,821
[45] Date of Patent: Nov. 7, 1995

[54] SMALL PEPTIDIC COMPOUNDS USEFUL FOR THE TREATMENT OF GLAUCOMA

[75] Inventors: Aasmul-Olsen Stig, Skodsborg, Denmark; Fred Widmer, Ryde, Australia; Kailash K. Gauri, Lentföhrden, Germany

[73] Assignee: Carlbiotech, Ltd., Denmark

[21] Appl. No.: 122,510

[22] PCT Filed: Mar. 25, 1992

[86] PCT No.: PCT/DK92/00095

§ 371 Date: Sep. 24, 1993

§ 102(e) Date: Dec. 16, 1993

[87] PCT Pub. No.: WO92/16551

PCT Pub. Date: Oct. 1, 1992

[30] Foreign Application Priority Data

Mar. 25, 1991 [DK] Denmark ................... 0532/91

[51] Int. Cl.$^6$ ............... A61K 38/00; C07K 5/00; C07K 7/00; C07K 17/00
[52] U.S. Cl. .................. 514/18; 514/19; 514/9; 514/11; 530/330; 530/331; 530/322; 536/17.2; 562/433; 564/161; 564/192; 558/154
[58] Field of Search .................. 530/328–331, 530/322; 514/15–19, 8, 9, 11; 536/17.2; 562/433; 564/161, 192; 558/154

[56] References Cited

U.S. PATENT DOCUMENTS

| | | | |
|---|---|---|---|
| 4,505,853 | 3/1985 | Goldstein et al. | 530/301 |
| 4,547,489 | 10/1985 | Goldstein et al. | 514/11 |
| 4,634,698 | 1/1987 | Andrews et al. | 514/223.2 |
| 5,081,021 | 1/1992 | Mizuno et al. | 435/69.5 |
| 5,223,486 | 6/1993 | Gordon et al. | 514/18 |
| 5,296,504 | 3/1994 | Stjernschantz et al. | 514/530 |

FOREIGN PATENT DOCUMENTS

| | | |
|---|---|---|
| 1315-85 | 3/1985 | Denmark . |
| 0088350B1 | 2/1985 | European Pat. Off. . |
| 0133225 | 8/1985 | European Pat. Off. . |
| 0174245 | 3/1986 | European Pat. Off. . |
| 0278787 | 8/1988 | European Pat. Off. . |
| 3200273 | 10/1982 | Germany . |
| 1420909 | 1/1976 | United Kingdom . |
| 86-04217 | 7/1986 | WIPO . |
| 03485 | 6/1987 | WIPO . |
| 91-09053 | 6/1991 | WIPO . |

OTHER PUBLICATIONS

Oya et al. Bull. Chem. Soc. Jpn. vol. 54 p. 2705 (1981).
Benditon et al. FEBS Lett. vol. 125 p. 104 (1981).
Easton et al Tet. Lett. vol. 29 p. 1565 (1988).
An Outline of Opthalmology, Coakes et al. (1985) pp. 54–57.
Fortschritte der Ophthalmologie, vol. 89 pp. 89–91 (1991). Abstract.
Antiglaucoma Agents, Sugrue et al., (1985) Ann. Repts. in Med. Chem. 20:83–91.
Norepinephrine, Epinephrine, and the Sympathomimetic Amines, Weiner, in The Pharmaceutical Basis of Therapeutics 6th, Goodman et al., (1980) pp. 138–155.
Peptides 1988, eds. Jung et al., Contents.
Evaluation of Mucoadhesive Polymers in Ocular Drug delivery, Davies et al., (1991) Pharaceutical Research 8:1039.
Tritiated D-ala-Peptide T Binding, Smith et al., (1988), Drug Develop. Res. 15371–379.
Biologically Active retro–inverson analogs of thymopentin, Sisto et al., (1990) in "Peptides, Chemistry, Structure and Biology," Escom, Leiden pp. 772—773.
Enzymatic Peptide Synthesis, Widmer et al., (1979) Carlsberg Res. Comm. 44:37–46.
Use of Proteolytic Enzymes in Peptide Synthesis, Widmer et al., (1985) in "Synthetic Peptides in Biology and Medicine," eds. Alitalo et al., pp. 79–86.
Adrenergica und neue peptide bei augeninnendruck: Beziehung zu prostaglandinen im kammerwasser von kaninchen, Steinbach, Thomas; Dissertation, Universitat Hamburg 1986.
Enzymatic Peptide Synthesis, (1987) Kullman, W. CRC Press, Boca Raton, Florida, Coverpage.

Primary Examiner—Jill Warden
Assistant Examiner—Sheela J. Huff
Attorney, Agent, or Firm—Banner & Allegretti, Ltd.

[57] ABSTRACT

Small peptidic compounds containing a small and branched chained amino acid residue, pharmaceutical compositions containing at least one such compound active against glaucoma and intraocular hypertension and a method for treating glaucoma and intraocular hypertension.

9 Claims, 4 Drawing Sheets

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: unknown     ( i i ) MOLECULE TYPE: peptide     ( i x ) FEATURE:
        ( A ) NAME/KEY: Modified-site
        ( B ) LOCATION: 1..5
        ( D ) OTHER INFORMATION: /note="Cys(Acm)-NH2"

( x i ) SEQUENCE DESCRIPTION: SEQ ID NO:1:

Asn  Gly  Gly  Val  Cys
    1                          5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: unknown     ( i i ) MOLECULE TYPE: peptide     ( i x ) FEATURE:
        ( A ) NAME/KEY: Modified-site
        ( B ) LOCATION: 1..5
        ( D ) OTHER INFORMATION: /note="Cys(Acm)-NH2"

( x i ) SEQUENCE DESCRIPTION: SEQ ID NO:2:

Asn  Leu  Gly  Val  Cys
    1                          5

( 2 ) INFORMATION FOR SEQ ID NO:3:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: unknown     ( i i ) MOLECULE TYPE: peptide     ( i x ) FEATURE:
        ( A ) NAME/KEY: Modified-site
        ( B ) LOCATION: 1..3
        ( D ) OTHER INFORMATION: /note="Val-OEt"

( x i ) SEQUENCE DESCRIPTION: SEQ ID NO:3:

Gly  Gly  Val
    1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: unknown     ( i i ) MOLECULE TYPE: peptide     ( i x ) FEATURE:
        ( A ) NAME/KEY: Modified-site
        ( B ) LOCATION: 1..4
        ( D ) OTHER INFORMATION: /note="Val-NH2"

( x i ) SEQUENCE DESCRIPTION: SEQ ID NO:4:

Asn   Gly   Gly   Val
    1

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: unknown     ( i i ) MOLECULE TYPE: peptide     ( i x ) FEATURE:
        ( A ) NAME/KEY: Modified-site
        ( B ) LOCATION: 1..4
        ( D ) OTHER INFORMATION: /note="Val-NH2"

( x i ) SEQUENCE DESCRIPTION: SEQ ID NO:5:

Asn   Leu   Gly   Val
    1

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: unknown     ( i i ) MOLECULE TYPE: peptide     ( i x ) FEATURE:
        ( A ) NAME/KEY: Modified-site
        ( B ) LOCATION: 1..4
        ( D ) OTHER INFORMATION: /note="Tyr-NH2"

( x i ) SEQUENCE DESCRIPTION: SEQ ID NO:6:

Asn   Leu   Gly   Tyr
    1

( 2 ) INFORMATION FOR SEQ ID NO:7:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: unknown     ( i i ) MOLECULE TYPE: peptide     ( i x ) FEATURE:
        ( A ) NAME/KEY: Modified-site
        ( B ) LOCATION: 1..3
        ( D ) OTHER INFORMATION: /note="Tyr-NH2"

( x i ) SEQUENCE DESCRIPTION: SEQ ID NO:7:

Gly Val Tyr
1

( 2 ) INFORMATION FOR SEQ ID NO:8:

( i ) SEQUENCE CHARACTERISTICS:
( A ) LENGTH: 3 amino acids
( B ) TYPE: amino acid
( C ) STRANDEDNESS: single
( D ) TOPOLOGY: unknown ( i i ) MOLECULE TYPE: peptide ( i x ) FEATURE:
( A ) NAME/KEY: Peptide
( B ) LOCATION: 1..3
( D ) OTHER INFORMATION: /note="Ac-Gly Gly Val-NH2"

( x i ) SEQUENCE DESCRIPTION: SEQ ID NO:8:

Gly Gly Val
1

( 2 ) INFORMATION FOR SEQ ID NO:9:

( i ) SEQUENCE CHARACTERISTICS:
( A ) LENGTH: 2 amino acids
( B ) TYPE: amino acid
( C ) STRANDEDNESS: single
( D ) TOPOLOGY: unknown ( i i ) MOLECULE TYPE: peptide ( i x ) FEATURE:
( A ) NAME/KEY: Peptide
( B ) LOCATION: 1..2
( D ) OTHER INFORMATION: /note="Where X is Benzylester
( O B z l ), Val- X"

( x i ) SEQUENCE DESCRIPTION: SEQ ID NO:9:

Gly Val
1

( 2 ) INFORMATION FOR SEQ ID NO:10:

( i ) SEQUENCE CHARACTERISTICS:
( A ) LENGTH: 2 amino acids
( B ) TYPE: amino acid
( C ) STRANDEDNESS: single
( D ) TOPOLOGY: unknown ( i i ) MOLECULE TYPE: peptide ( i x ) FEATURE:
( A ) NAME/KEY: Peptide
( B ) LOCATION: 1..2
( D ) OTHER INFORMATION: /note="Where X is Benzylester
( O B z l ) and Z- Ala is beta-alanine, Z-Ala Val-X"

( x i ) SEQUENCE DESCRIPTION: SEQ ID NO:10:

Ala Val
1

( 2 ) INFORMATION FOR SEQ ID NO:11:

( i ) SEQUENCE CHARACTERISTICS:
( A ) LENGTH: 3 amino acids
( B ) TYPE: amino acid
( C ) STRANDEDNESS: single
( D ) TOPOLOGY: unknown -continued (i i) MOLECULE TYPE: peptide (i x) FEATURE:
    (A) NAME/KEY: Peptide
    (B) LOCATION: 1..3
    (D) OTHER INFORMATION: /note="Cys(Acm)-NH2"

(x i) SEQUENCE DESCRIPTION: SEQ ID NO:11:

Gly Val Cys
1

(2) INFORMATION FOR SEQ ID NO:12:

(i) SEQUENCE CHARACTERISTICS:
        (A) LENGTH: 3 amino acids
        (B) TYPE: amino acid
        (C) STRANDEDNESS: single
        (D) TOPOLOGY: unknown (i i) MOLECULE TYPE: peptide (i x) FEATURE:
        (A) NAME/KEY: Peptide
        (B) LOCATION: 1..3
        (D) OTHER INFORMATION: /note="Ac-Gly Val Cys(Acm)-NH2"

(x i) SEQUENCE DESCRIPTION: SEQ ID NO:12:

Gly Val Cys
    1

(2) INFORMATION FOR SEQ ID NO:13:

(i) SEQUENCE CHARACTERISTICS:
        (A) LENGTH: 3 amino acids
        (B) TYPE: amino acid
        (C) STRANDEDNESS: single
        (D) TOPOLOGY: unknown (i i) MOLECULE TYPE: peptide (i x) FEATURE:
        (A) NAME/KEY: Peptide
        (B) LOCATION: 1..3
        (D) OTHER INFORMATION: /note="Cys(Acm)-NH2"

(x i) SEQUENCE DESCRIPTION: SEQ ID NO:13:

Asn Val Cys
    1

(2) INFORMATION FOR SEQ ID NO:14:

(i) SEQUENCE CHARACTERISTICS:
        (A) LENGTH: 2 amino acids
        (B) TYPE: amino acid
        (C) STRANDEDNESS: single
        (D) TOPOLOGY: unknown (i i) MOLECULE TYPE: peptide (i x) FEATURE:
        (A) NAME/KEY: Modified-site
        (B) LOCATION: 1..2
        (D) OTHER INFORMATION: /note="Boc-Gly Val-Obzl"

(x i) SEQUENCE DESCRIPTION: SEQ ID NO:14:

Gly Val
    1

SMALL PEPTIDIC COMPOUNDS USEFUL FOR THE TREATMENT OF GLAUCOMA

BACKGROUND OF THE INVENTION

1. Field of the Invention

The present invention relates to small peptidic compounds, pharmaceutical preparations containing such compounds and a method for treating glaucoma.

2. Description of the Prior Art

Glaucoma is a very common eye disease affecting millions of people in the later stages of their life. Glaucoma is characterized by abnormally high intraocular pressure and, if untreated, damage to the optic nerves which may cause narrowing of the visual field, and eventually irreversible blindness.

The intraocular pressure is determined by the rates of inflow and outflow, i.e. the dynamics of the aqueous humour. The aqueous humour enters into the posterior chamber of the eye, and then flows through the pupil to the anterior chamber, from where it eventually leaves the eye through the trabecular meshwork.

The aqueous humour supplies nutrients to the lens and cornea, and its proper supply is thus of the utmost importance for maintaining healthy eyes.

Any disturbance of aqueous humour dynamics by either excess inflow, or reduced outflow, results in an increase in the intraocular pressure above the normal value (for adults) of 17–20 mm Hg, i.e. the eye becomes hypertensive. A prolonged hypertensive state will result in nerve damage and blindness. Detailed descriptions on glaucoma can be found in "An Outline of Ophthalmology", by R. L. Coakes, and P. J. Holmer Sellars, published by Wright, Bristol (1985), cf. pp. 54/57, and in the series: Current Topics in Eye Research", edited by J. A. Zadunaisky and K. Davson, Academic Press.

All known antiglaucoma drugs on the market lower the intraocular pressure, either by decreasing formation of aqueous humour, or by increasing the outflow, i.e. the elimination of aqueous humour from the eye. Glaucoma drugs are thus all hypotensive agents.

The most common class of antiglaucoma agents are adrenergic antagonists; many of them are β-blockers (the most widely used of this type is timolol), adrenergic agonists, dopaminergic agents, cholinergic agents (the most widely used of this type is pilocarpine), or several other classes of compounds. For detailed overviews, see for example Annual Reports in Medicinal Chemistry, Vol. 20, chapter 9: "Antiglaucoma Agents", by M. F. Sugrue and R. L. Smith (1985, Academic Press), and the text: "The Pharmacological Basis of Therapeutics" by A. Goodman and L. Gilmans.

Thus one of the characteristics of glaucoma theory is the fact that an enormous variety of chemical structural types can be used to reduce excessively high intraocular pressure.

None of the currently used drugs is fully satisfactory. There are serious side effects affecting the heart, the kidneys, the lungs and/or the libido. Some of the side effects are, especially in the case of carbonic anhydrase inhibitors, α-adrenergic antagonists and β-adrenergic antagonists, directly implicated with the different modes of action, while others are not. Furthermore, there are problems of metabolic stability which necessitates several applications of eye drops per day. Great efforts are therefore made to develop new antiglaucoma agents which would be free of the above constraints. Recently, an entirely new chemical structural type of compounds, namely peptides and peptide derivatives, was described as having antiglaucoma activity, i.e. as hypotensive agents. Examples are carboxyalkyl dipeptides (European Patent No. 0088350) and the atrial natriuretic factor, a long peptide of 29 amino acids in length (Fortschritte der Ophthalmologie, Volume 89, pp. 89/91 (1989)).

U.S. Pat. No. 4,634,698 describes ophthalmological pharmaceutical compositions comprising carboxyalkyl dipeptides joined through a sulfonamido group to a benzothiadiazinyl sulfonylphenyl moiety and to a method for using said composition in the treatment of glaucoma. The compositions contain as active agent cyclic, proline-type amino acids, which differ substantially from the compounds according to the invention. Besides the peptide moiety being different from the one in the compounds claimed in the present invention the known compounds further obligatorily contain sulfonamido groups. The sulfonamido group is also present in the older antiglaucoma drug acetazolamide which is a carbonic anhydrase inhibitor.

Danish Patent Application No. 1315/85, which has lapsed, discloses a process for treatment of glaucoma and/or intraocular hypertension by using ACE inhibitors. The ACE inhibitors mentioned were said to be useful also for lowering high blood pressure of different genesis. However, the proposed ACE inhibitors are not of the type proposed in the present invention since they as one of the two amino acids contain one in which the α-amino group and the side chain together obligatorily form an at least C4 heterocyclic ring system. Further it is not rendered possible that the compounds have the claimed effect.

Furthermore, hydrolysates of milk proteins were also described as having antiglaucoma activity (WO 86/04217 and EP 210204). The peptide compositions described therein are not well defined chemical compounds as are the compounds of the present invention, rather they are mixtures which resulted from the hydrolysis of milk proteins.

The applicants' previous patent application No. PCT/DK90/00322, filed on Dec. 7, 1990, concerns peptide derivatives of the formula $$R_1—A—B—C—D—E—R_2 \quad\quad I$$

wherein

A is absent or is a non-hydrophobic, uncharged amino acid or a derivative thereof, B is absent or is an uncharged amino acid or an uncharged N-methylated amino acid, C is an uncharged amino acid or an uncharged N-methylated amino acid, D is an uncharged amino acid with a non-hydrophilic or absent side chain, E is cysteine or a cysteine homologue, the sulfhydryl group being free or substituted, $R_2$ is optionally substituted $NH_2$, optionally substituted OH, —O-glycosyl, an L- or D-α-amino acid, or $R_2$ is absent.

These compounds are active with glaucoma and intraocular hypertension. Preferred compounds are H-Asn-Gly-Gly-Val-Cys(Acm)-$NH_2$ (SEQ ID NO.1) and H-Asn-Leu-Gly-Val-Cys(Acm)-$NH_2$ (SEQ ID NO.2). One of the compounds has been tested on human beings and has proved itself suitable against glaucoma and intraocular hypertension by topical application, while no side effect was found on blood pressure or heart rate. The absence of these cardiovascular effects of this compound has also been demonstrated by i.v. administration in rats.

It has now surprisingly been found that smaller entities of such a parent compound of dipeptidal structure may in themselves be active core structures. As another such class of minimal structures which are significantly different (see the concurrently filed DK patent application No. 0531/91) has been identified, both the mode of action, metabolism and possible side effect profiles may be envisaged to be different. Thus the separation of these new core structures from the parent structure may constitute a significant advantage as a base for design of optimal pharmaceutical preparations targeted specifically towards different forms of glaucoma, treatment profiles and patient groups, while further reducing risk of side effects.

The present invention relates to compounds with dipeptidal structure, and derivatives thereof, which lower the intraocular pressure, IOP, in relevant animal models.

SUMMARY OF THE INVENTION

The compounds of the invention are of the general formula or an ω-amino-α-carboxy cyclic form thereof, or a compound transformed into or releasing any of the above basic structures under physiological conditions in humans, wherein $R_1$ is H, or where R is H, straight, branched alkyl or cycloalkyl up to $C_{20}$, optionally containing double bonds and/or substituted with halogen, nitro, amino, sulfo, phospho or carboxyl, or aralkyl or aryl optionally mono- or polysubstituted with halogen, hydroxy, nitro, amino, sulfo, phospho, carboxy or alkyl, or R or $R_1$ is glycosyl, nucleosyl, or $R_1$ is an L- or D-α amino acid or a peptide moiety of 2 to 8 residues, connected by bonds of type [P], F is or absent wherein $R_1'$ is as defined for $R_1$ and is absent, when the compound is an N—C-cyclic form, a is 0, 1 or 2, $C_x$ and $C_y$ are tetrahedral carbon atoms (SP3 hybridized) independently having R or S configuration or $C_x$ is achiral, $C_z$ is a triplanar carbon atom (SP2 hybridized) and D is absent or $C_z$ is a tetrahedral carbon atom and D is $H_2$, A is H or $CH_3$, B is with respect to $C_y$ α- or β-branched $C_3$–$C_7$ alkyl or $C_4$–$C_7$ cycloalkyl, or phenyl or benzyl,

[P] is a peptide bond CO—NH, substituted forms thereof, e.g. CO—$NR_6$, wherein $R_6$ is $C_1$–$C_3$ alkyl, or isosteres thereof such as $CH_2$—NH, $CH_2$—S, CO—$CH_2$, retroinverse forms thereof, such as NH—CO, $R_2$ is H, OH, NH—$NH_2$, NHOH or $NR_3R_4$, wherein $R_3$ and $R_4$ are independently H, straight or branched alkyl or cycloalkyl, aralkyl or aryl optionally mono- or polysubstituted with halogen, carboxy, sulfo, phospho, amino or nitro, $OR_5$, where $R_5$ is H, straight or branched alkyl or cycloalkyl, aralkyl or aryl, optionally substituted as defined for $R_3$ and $R_4$, O-glycosyl, or an L- or D-α-amino acid or a peptide moiety of 2 to 8 residues, or $R_2$ is absent when the compound is an N—C cyclic form, b is 1, 2, 3 or 4, and $R_1$ and $R_2$ together comprise no more than 10 amino acid residues, and wherein hydrogen atoms may be replaced by fluorine, or a derivative or salt thereof.

DESCRIPTION OF THE PREFERRED EMBODIMENTS

Preferred compounds of the invention are of the general formula wherein C is Gly, β-Ala, Ala or GABA, G is Val, Ile, tert.Leu, Leu, Tyr, Phe or cyclohexylalanin, in L-configuration, and [P], b, $R_1$ and $R_2$ are as defined in claim 1, except that $R_2$ cannot be Cys or Cys-homologues, or a derivative or salt thereof.

Especially preferred compounds contain the sequence C'-Val wherein C' is β-Ala or Gly.

Examples of active compounds are

| | |
|---|---|
| H-Gly-Gly-Val-OEt, | (SEQ ID NO.3) |
| H-Asn-Gly-Gly-Val-NH$_2$, | (SEQ ID NO.4) |
| H-Asn-Leu-Gly-Val-NH$_2$, | (SEQ ID NO.5) |
| H-Asn-Leu-Gly-Tyr-NH$_2$, | (SEQ ID NO.6) |
| H-Gly-Val-Tyr-NH$_2$, | (SEQ ID NO.7) |
| Ac-Gly-Gly-Val-NH$_2$ | (SEQ ID NO.8) and |
| H-Gly-Val-OBzl | (SEQ ID NO.9) |

H-β-Ala-Val-OBzl          (SEQ ID NO.10)

and derivatives or salts thereof.

A number of small peptides which contain some of the basic substructures belonging to the class of compounds defined in the present invention are known, see e.g. WO 87/03485, WO 90/14358, EP 0133225, EP 0174245, EP 0188629, EP 89485, EP 0278787, EP 0410372, DE 3200273, DE 3412445, DE 3544375, GB 1420909, Patent Abstract of Japan, 11, 133, Patent Abstract of Japan, 8, 251, and Tetrahedron Letters, 29, (1988): 13, pp. 1565–1568. None of the compounds disclosed are said to have antiglaucoma effect.

Especially effective peptides for treating glaucoma and intraocular hypertension are H-Gly-Val-Benzylester          (SEQ ID NO.9) and H-β-Ala-Val-Benzylester        (SEQ ID NO.10)

These novel peptides and their structurally related active derivatives are described in claim 1.

Further, the invention relates to a pharmaceutical composition containing a compound according to the invention in an amount effective to treat glaucoma or intraocular hypertension and a pharmaceutically acceptable diluent or excipient.

Additionally, the invention relates to a method for treating glaucoma or intraocular hypertension, comprising administering to a mammal an effective antiglaucoma or intraocular pressure lowering amount of a peptide derivative according to the invention.

The peptide derivatives of this invention are preferably used in topically applicable aqueous isotonic and sterile solutions or in sterile solutions or dispersions in an oil as used for the topical treatment of the eye. A typical oil for ocular treatment is sterile castor oil. These topical solutions or dispersions contain 0.01–10%, in particular 0.1–5%, preferably 0.25–1% (percent by weight) of at least one of the peptide derivatives of this invention. The normal dosage of these solutions is 1 to 5 drops administered to the conjunctival sac of the eye. This dosage is normally administered 2 to 6 times per day. [20 drops of a DAB-9 dropper (Tropfenzähler gemäss "Deutsches Arzneibuch 9") will give about 1 ml].

In the present invention the term amino acid is to be understood to not only cover the 20 natural amino acids, but also to embrace amino acid replacements and substituents as recognized in the art.

The term alkyl is to be understood to cover all saturated hydrocarbons as exemplified in e.g. IUPAC. As examples are mentioned methyl, ethyl, n-propyl, isopropyl, n-butyl, isobutyl and tert.-butyl for $C_1$–$C_4$ alkyl. In similar way the term aryl is as defined in e.g. IUPAC, and halogen means chlor, brom, iod or fluor.

The term peptide is to be understood to embrace peptide bond replacements and/or peptide mimics, i.e. pseudopeptides, as recognized in the art (see for example: Proceedings of the 20th European Peptide Symposium, eat. G. Jung, E. Bayer, pp. 289–336, and references therein), as well as salts and pharmaceutical preparations and/or formulations which render the bioactive peptide(s) particularly suitable for topical application as drops, or for oral delivery. Such salts, formulations, amino acid replacements and pseudopeptide structures may be necessary and desirable to enhance the stability, formulation, deliverability, or to improve the economy of production, and they are acceptable, provided they do not negatively affect the required biological activity of the peptide as a hypotensive agent suitable for lowering of elevated intraocular pressure and glaucoma.

The actual pharmacological activity effects are envisaged as mediated through binding of the structurally active center(s) of the molecules to one or more hitherto unestablished and perhaps unknown receptors in the eye. Thus, so far no receptor displacement, in vivo or in vitro, assays performed on the compound HAsnLeuGlyValCys(Acm)$NH_2$ (SEQ ID NO.2), a potent compound according to PCT DK90/00322, has been able to demonstrate any α-adrenergic agonistic or β-adrenergic antagonistic effects, cholinergic effects or carbonic anhydrase inhibitory effects.

The pharmacological efficacy, potency and duration of effect may be modulated through additional structural features, such as chain elongation, optical isomerism, the substitution of peptide bond isosters, or substitution with one or more groups, which in case of susceptibility to enzymatic or spontaneous chemical conversion under the pharmacological conditions may also constitute prodrug forms. Different additives and vehicles may also affect pharmacokinetic and therapeutic effects.

The modulation may in some cases lead to significant improvement of performance because of enhanced stability, eye penetration, transport to the receptor, or controlled release. An example of the-use of amino acid and N-terminal substitutions to enhance stability is given in "Enzyme resistant immunomodulatory peptides" U.S. Pat. No. 4,505,583 (1985), Goldstein, G. et al. An example of peptide prodrugs is mentioned in Int. J. of Pharmaceutics 52, p. 255 (1989), Bundgaard, H. An example of the use of additives is given in "Evaluation of mucoadhesive polymers in ocular drug delivery. 1. Viscous solutions", Pharmaceuticals Res. 8, p. 1039 (1991), Davies, N. M. et al.

Apart from substitutions, three particular forms of peptide mimetic and/or analogue structures of particular relevance when designing bioactive peptides, which have to bind to a receptor while risking the degradation by proteinases and peptidases in the blood and elsewhere, may be mentioned specifically, illustrated by the following examples: Firstly, the inversion of backbone chiral centers leading to D-amino acid residue structures may, particularly at the N-terminus, lead to enhanced stability for proteolytic degradation while not impairing activity. An example is given in the paper "Tritiated D-Ala$^1$-Peptide T Binding", Smith, C. S. et al, Drug Development Res. 15, pp. 371–379 (1988). Secondly, stability and sometimes also receptor binding may be enhanced by forming cyclic analogues. An example of this is given in "Conformationally restricted thymopentin-like compounds", U.S. Pat. No. 4,547,489 (1985), Goldstein, G. et al. Finally, the introduction of ketomethylene, methylsulfide or retroinverse bonds to replace peptide bonds, i.e. the interchange of the CO and NH moieties may both greatly enhance stability and potency. An example of the latter type is given in the paper "Biologically active retroinverso analogues of thymopentin", Sisto A. et al in Rivier, J. E. and Marshall, G. R. (eds.) "Peptides, Chemistry, Structure and Biology", Escom, Leiden (1990), p. 722–773.

A more closely related example of modulation of effect by structural modification not related directly to receptor binding is taken from PCT/DK90/00322 in which the pentapeptide HAsnLeuGlyValCys(Acm)$NH_2$ (SEQ ID NO.2) was shown both to penetrate the sclera of the eye and to be a potent pressure lowering agent. It further contains two activity centers, one according to the present application and one according to the concurrently filed DK patent application No. 0531/91 together forming the tripeptide moiety-GlyValCys(Acm)$NH_2$ (SEQ ID NO.11). However, when the corresponding particular N-α-unprotected tripeptide HGly-ValCys(Acm)NH$_2$ (SEQ ID NO.11) was tested in the stress induced rabbit model for antagonizing effect, this was found to be significantly lower than expected. However, merely acetylating the tripepride to AcGlyValCys(Acm)NH$_2$ (SEQ ID NO.12) partially restored activity. Parallel studies, e.g. on HAsnValCys(Acm)NH$_2$ (SEQ ID NO.13) and HGly-ValOBzl (SEQ ID NO.9), have shown that the lower efficacy is not due to the free amino terminus per se, since these had a good efficacy. Without wanting to be committed to one particular theory, it may be speculated that the overall amphiphilicity of the molecule by acetylation in case of HGlyValCys(Acm)NH$_2$ (SEQ ID NO.11) is made more favourable, thus improving penetration and transport through the eye and/or to the receptor. Some enhanced enzymatic stability may also be envisaged from the acetylation.

The peptides of the invention can be synthesized by various methods which are known in principle, namely by chemical coupling methods (cf. Wunsch, E.: "Methoden der organischen Chemie", Volume 15, Band 1+2, Synthese yon Peptiden, Thieme Verlag, Stuttgart (1974), and Barrany, G.; Merrifield, R. B.: "The Peptides", eds. E. Gross, J. Meienhofer., Volume 2, Chapter 1, pp. 1–284, Academic Press (1980)), or by enzymatic coupling methods (cf. Widmer, F., Johansen, J. T., Carlsberg Res. Commun., Volume 44, pp. 37–46 (1979), and Kullmann, W.: "Enzymatic Peptide Synthesis", CRC Press Inc., Boca Raton, Fla. (1987), and Widmer, F., Johansen, J. T. in "Synthetic Peptides in Biology and Medicine", eds., Alitalo, K., Partanen, P., Vatieri, A., pp. 79–86, Elsevier, Amsterdam (1985)), or by a combination of chemical and enzymatic methods if this is advantageous for the process design and economy.

The peptide derivatives of the invention can be produced by the above listed general synthetic methods, or by an advantageous combination thereof.

The described peptides which constitute this invention can be used for the treatment of glaucoma in pharmaceutical preparations, possibly in combination with pharmaceutical carriers and delivery systems and/or other useful and pharmaceutically acceptable additives.

It was shown in an animal experiment where the intraocular pressure, IOP, in the rabbit eye was experimentally raised above the normal level, that the compounds of the invention were able to achieve a lowering of the intraocular pressure in a similar way as when timolol was applied. Timolol is commonly used to treat glaucoma, but, however, being a β-blocker, it has serious side effects on the heart, lungs and/or sexual functions.

It is anticipated that with the compounds according to the invention, many of these and other side effects can be avoided. Indeed, a particular pentapeptide according to PCT/DK90/00322 containing a characteristic structure of the compounds according to the invention, HAsnLeuGlyValCys(Acm)NH$_2$ (SEQ ID NO.2), has been especially thoroughly examined for side effects, especially blood pressure and heart rate effects, toxicity and mutagenicity as well as local irritant or anaesthetic effects in a variety of animal and microbial models.

The animal model on which the IOP lowering effect of the antiglaucoma compound(s) was first established, is a clinically relevant model which was developed in the laboratory of one of the inventors who has positively shown in this model the pressure lowering effect of many β-blockers (such as timolol) and adrenergic agonists, and thus has demonstrated the clinical relevance of the model on known and putative glaucoma drugs.

The main feature of this clinical model is a stress induced elevation of the IOP in the rabbit eye above the initial and normal value. The stress is exerted, i.e. applied, in the form of measuring the pressure (at 12 hour intervals) with the help of a SHIOTZ-Tonometer, which is loaded with 7.5 grams. The pressure first begins to rise after 5 measurements, i.e. after 2½ days, and reaches a maximum after 10 measurements, i.e. after 5 days.

Known antiglaucoma drugs lower the intraocular pressure when they are applied after the intraocular pressure (IOP) has clearly been established, in spite of the fact that the trauma, i.e. the measuring of the pressure, continued during the treatment.

If the treatment with the antiglaucoma drugs is started simultaneously with the traumatization, i.e. the exertion of stress by measuring of the pressure at the start of the animal experiment, the active antiglaucoma drugs antagonize the development of an elevated IOP above the initial and normal value, while the inactive compounds will not antagonize, and thus result in an elevated pressure. The relevance of this model has been demonstrated in many experiments with clinically used antiglaucoma drugs.

Detailed description of the model is found in: Stainbach, T., Dissertation, Universitäts-Augenklinik Hamburg-Eppendorf, 1986: "Adrenergica und neue Peptide bei Augeninnendruck: Beziehung zum Prostaglandin im Kammerwasser yon Kaninchen".

The IOP activity of the compounds of the present invention has likewise been demonstrated on this model as shown in the examples. These peptidic compounds are thus likely candidates for the treatment of glaucoma.

The peptide compositions described in the above doctoral thesis are as mentioned not well defined chemical compounds as are the peptide derivatives of this invention, rather they are mixtures which resulted from the hydrolysis of milk proteins. These peptides and their various activities, among which is antiglaucoma, are described in the European Patent No. 210 204 by one of the present inventors.

The findings of IOP lowering effects in the stress induced rabbit model have been confirmed and further studied by using another elevated eye pressure rabbit model. In this model, the widely applied water load model, elevation of the intraocular pressure is achieved by injecting a large volume of sterile water intraperitoneally into the rabbits. Following onset of eye drop treatment in one eye while the other eye is treated with saline placebo, the intraocular pressure of both eyes is then measured at various intervals and the pressure difference between the eyes is taken as an expression of the pharmaceutical effect. In this model pilocarpine, a well-known pressure lowering cholinergic agent, was shown to have a pressure lowering effect.

The advantage of the compounds of the invention is their defined chemical nature, Which allows for proper registration and, if deemed desirable, for logic and systematic structural modification to produce analogues of even better properties than the ones invented and claimed now.

Furthermore, the compounds according to the invention are of low molecular weight ($\leq 800$), and thus topically applicable, unlike the atrial natriuretic factor described in Fortschritte der Ophthalmologie, Volume 86, p. 89–91 (1989), which has a molecular weight of ~3000, and needs to be administered by injection to achieve an antiglaucoma effect.

Moreover, the atrial natriuretic factor is a cardiovascular hormone and thus not suited to be used for treatment of glaucoma over prolonged periods of time. Finally, both the peptidic protein hydrolysate mixtures (which are not necessarily strictly peptidic in chemical structural terms) and the atrial natriuretic factor are of a size which may give rise to an immune response followed by the production of antibodies. Such a response is unlikely to occur with the low molecular weight compounds according to the invention.

The mechanism, or mechanisms, by way of which the peptides according to the invention work, is so far not known in detail and may be of hitherto unknown types or related to some known mechanisms. With the apparent lack of β-blocking effects, α-agonistic effects, cholinergic effects and inhibitory effects on the enzyme carbonic anhydrase other effects on aqueous humour outflow could be working. Some indications of mechanisms of the latter type have been found in in vitro studies. Thus, an in vitro study conducted at an early stage demonstrated that the parent compound HAsnGlyGlyValCys(Acm)NH$_2$ (SEQ ID NO.1) induced a marked and significant decrease of uptake of glycosamines in cultured bovine trabecular meshwork cells. From this decrease in the synthesis of glucosamineglycanes of importance in the outflow resistance was inferred.

The invention is now further explained and documented by way of examples.

PHARMACOLOGICAL EXAMPLES

Antagonizing of the Intraocular Pressure in the stressed Rabbit's Eyes Model

The compound lowers the experimentally increased IOP in the rabbit animal model, or it antagonizes, i.e. prevents the increase in pressure when it is applied simultaneously with the treatment which inflicts the increase in the pressure.

The compound was a freeze-dried powder, and was applied to the rabbit eye as a powder, or as drops, dissolved in 0.9% NaCl aqueous solution. Negative control was 0.9% NaCl solution in water.

Water Load Model Effects in Rabbit's. Eyes

The studies utilized a "water load" animal model.

Thirty minutes before drug solution instillation, rabbits were injected intraperitonally with 60 ml/kg of sterile distilled water for injection (30° C.) spiked with an antibiotic mixture (Sigma P9032).

At time zero, 50 μl of a drug solution was instilled to one eye and an equal volume of a saline solution was instilled to the other eye. The IOP in each eye was monitored at the time points indicated. The change in IOP at each time point is computed by subtracting the IOP in the dosed eye from that in the undosed-eye.

Plots of this data were made showing the IOP versus time including standard deviation. From these plots were assessed the maximal IOP effect, the time to reach this and the time for returning to a zero or insignificant level of IOP lowering effect. These figures were taken as a measure of potency and duration of effect.

General note for pharmacological examples 1–6

Peptides were tested for the intraocular pressure lowering or antagonizing effects in the water load model described above or the stress induced antagonizing model respectively, in groups of four to ten rabbits, as described below. The tests were performed on homogeneous groups of randomly sexed rabbits, weight 2.5–3.0 kg, but of different breeds in various laboratories several places in the world. Thus, in some cases intergroup variations were found in the absolute starting pressure of the rabbit's eyes.

In the case of the water load model structure, each rabbit served as its own reference control for the duration of the experiment, and in the case of the stress induced antagonistic model, each group of rabbits served as reference control, at the beginning and end of 10 stress units. Usually, the peptides were dissolved in plain isotonic saline, but in one case in the waterload model, a TRIS-buffer at physiological pH was included.

Figure 4:
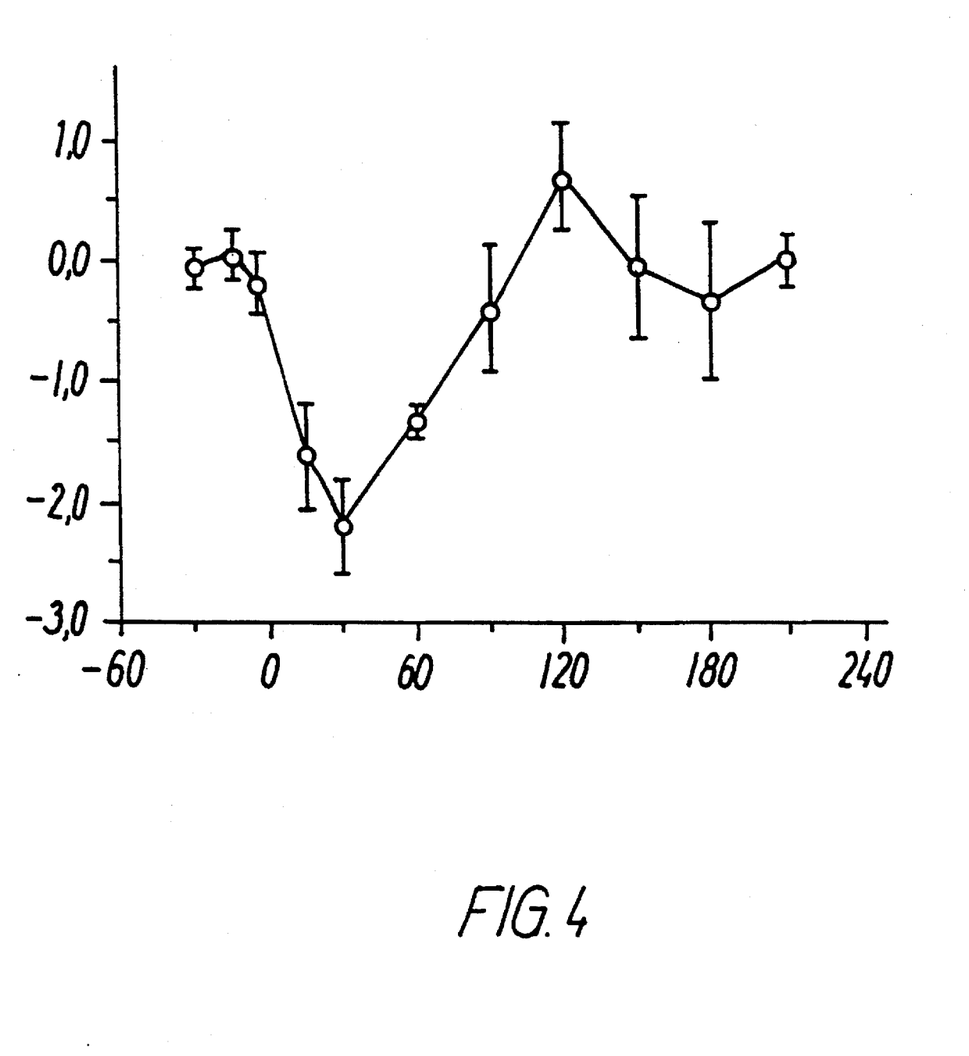
FIG. 4 is a graph of the change in the intraocular pressure as a function of time for the reference control, pilocarpine.

In both cases a negative saline control group showed no effect on the pressure. The relevant TRIS-buffer control group showed also no effect in the waterload model, while a 2.6% solution of the known miotic glaucoma drug, pilocarpine, gave a similar response to some of the preferred compounds as illustrated in the drawing of FIG. 4. The compounds listed in the tables were then classified as active on the following criterion: In the water load model one drop of a 1% solution in one eye resulted in a significant pressure lowering effect corresponding to the control treated eye, which was at maximum at least 1 mm Hg within 1 hour and with a lowering effect duration of at least 90 minutes for the group on average. In the stress induced antagonizing model, the pressure increase following 10 stress units for the treated group on average was found to be smaller than 2 mm Hg and to be significantly less compared to untreated controls, which normally gave 8 to 18 mm Hg.

The following examples are further explained by means of the drawing in which

Figure 1:
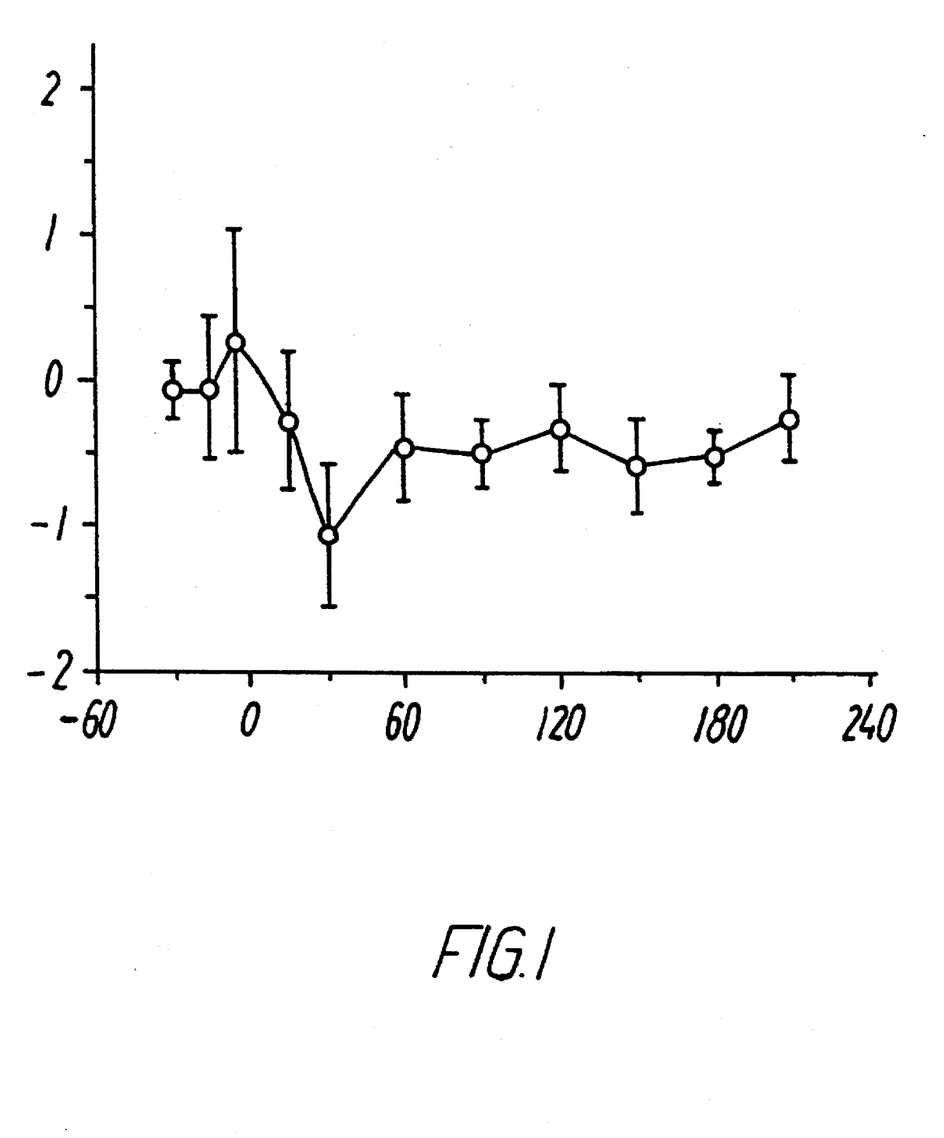
FIG. 1 is a graph of the change in the intraocular pressure as a function of time for the peptide AcGlyGlyValNH$_2$.
Figure 2:
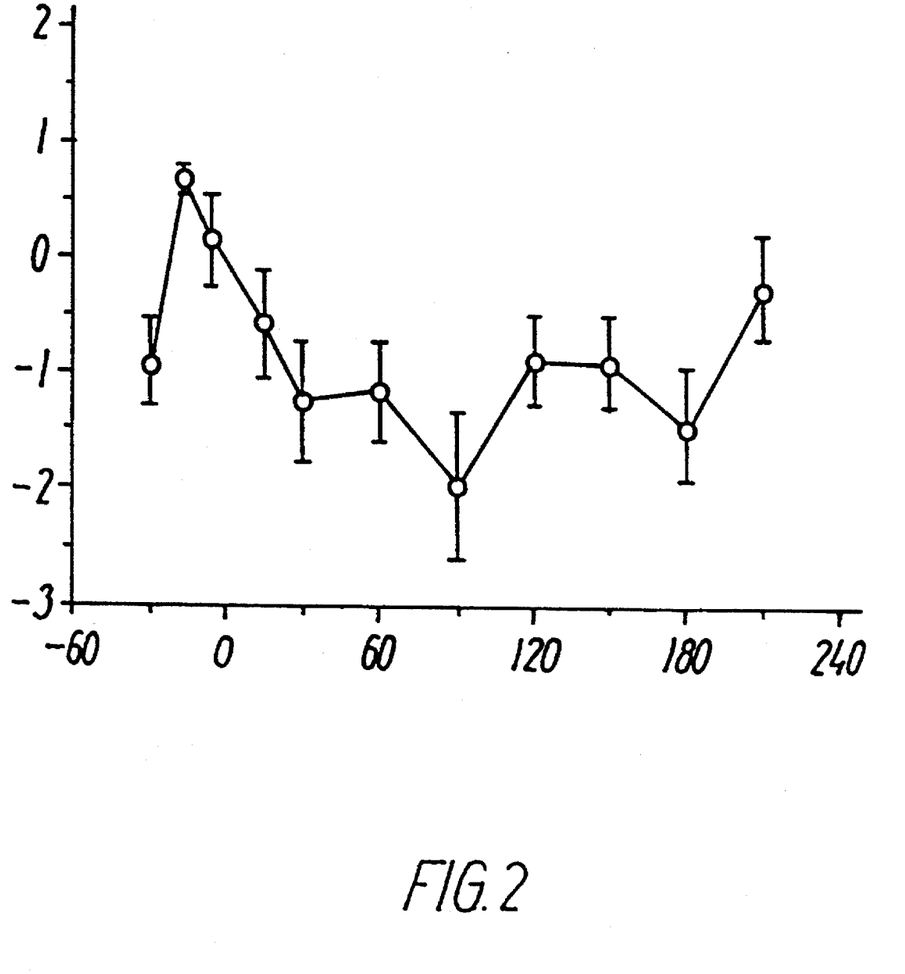
FIG. 2 is a graph of the change in the intraocular pressure as a function of time for the peptide HGlyValOBzl.
Figure 3:
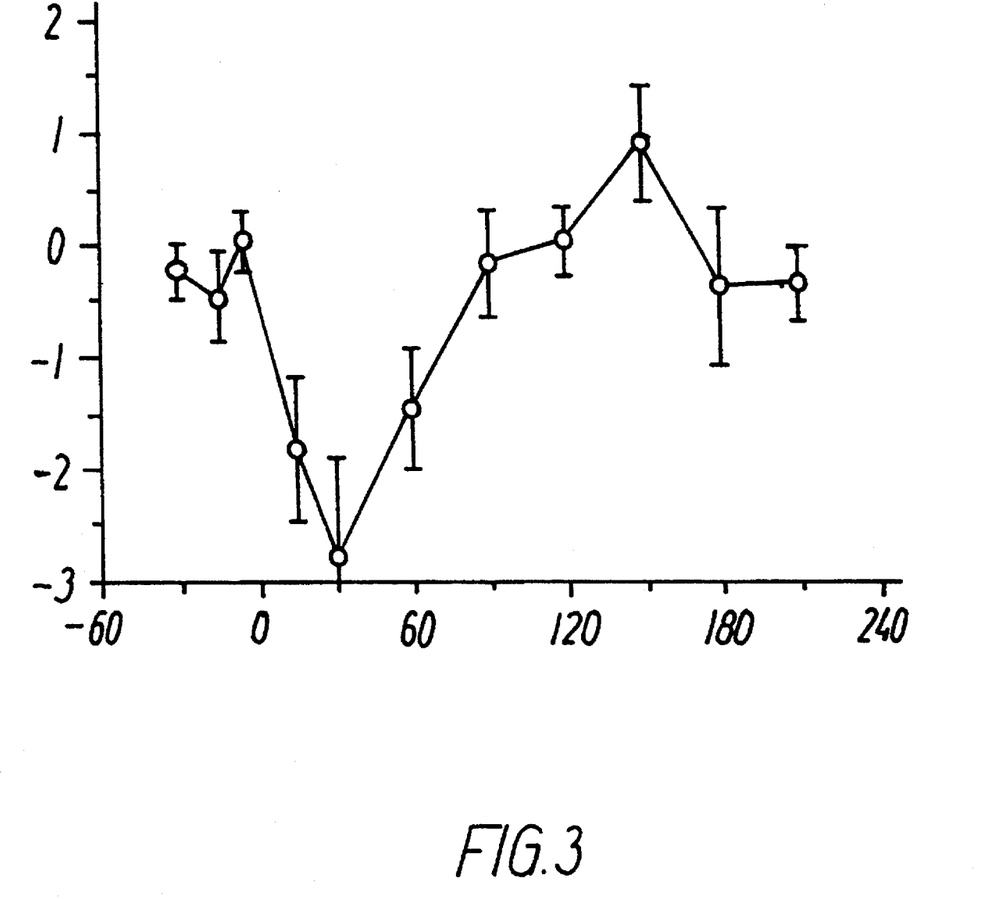
FIG. 3 is a graph of the change in the intraocular pressure as a function of time for the peptide H-β-Ala-Val-OBzl.

FIG. 1 shows the change in the intraocular pressure, ΔIOP, in mm Hg as a function of the time in minutes for the compound Peptide 3, 1%, AcGlyGlyValNH$_2$ (SEQ ID NO.8), FIG. 2 shows the change in the intraocular pressure, ΔIOP, in mm Hg as a function of the time in minutes for the compound Peptide 1.4, 1%, HGlyValOBzl (SEQ ID NO.9), FIG. 3 shows the change in the intraocular pressure, ΔIOP, in mm Hg as a function of the time in minutes for the compound Peptide No. 109, 1%, H-β-Ala-Val-OBzl (SEQ ID NO.10), and FIG. 4 shows the change in the intraocular pressure, ΔIOP, in mm Hg as a function of the time in minutes for the positive reference control 2,6% pilocarpine.

EXAMPLE 1

Antagonizing effect of tri- and tetrapeptides containing the sequence Gly-Gly-Val with various N- and C-substitutions on the stress induced intraocular pressure in the rabbit's eye, following 10 stress units.

The peptides were applied topically as a 1% solution in 0.9% aqueous NaCl in aliquots of 60 μl 3 times daily over a period of 5 days.

| Peptide | Antagonizing Effect |
| --- | --- |
| H-Gly-Gly-Val-OEt | Active |
| H-Asn-Gly-Gly-Val-NH$_2$ (SEQ ID NO. 9) | Active |

EXAMPLE 2

Antagonizing effect of tetrapeptides containing the sequence Asn-Leu-Gly-X-NH$_2$, where X is Val or Tyr, on the stress induced IOP in the rabbit's eye, following 10 stress units.

The peptide was applied topically as a 1% solution in 0.9% aqueous NaCl in aliquots of 60 μl 3 times daily over a period of 5 days.

| Peptide | Antagonizing Effect |
| --- | --- |
| H-Asn-Leu-Gly-Val-NH$_2$ (SEQ ID NO. 5) | Active |
| H-Asn-Leu-Gly-Tyr-NH$_2$ (SEQ ID NO. 6) | Active |

EXAMPLE 3

Antagonizing effect of tripeptides containing the sequence Gly-Val on the stress induced intraocular pressure in the rabbit's eye, following 10 stress units.

The peptides were applied topically as a 1% solution in 0.9% aqueous NaCl in aliquots of 60 μl 3 times daily over a period of 5 days.

| Peptide | Antagonizing Effect |
| --- | --- |
| H-Gly-Val-Tyr-NH$_2$ (SEQ ID NO. 7) | Active |
| Ac-Gly-Gly-Val-NH$_2$ (SEQ ID NO. 8) | Active |

EXAMPLE 4

Pressure lowering effect of tripeptides containing the sequence Gly-Val on water load induced hypertension in the rabbit's eye by single dose treatment.

50 μl of a 1% solution of the peptides in 0.9% aqueous saline were applied in one eye and 50 μl of 0.9% aqueous saline in the other eye 30 minutes after the intraperitonal water loading and IOP were measured in both eyes for 2 hours and the difference calculated.

| Peptide | Pressure Lowering Effect |
| --- | --- |
| H-Gly-Val-Tyr-NH$_2$ (SEQ ID NO. 7) | Active |
| Ac-Gly-Gly-Val-NH$_2$ (SEQ ID NO. 8) | Active |

The time curve for the pressure lowering effect in the waterload model for AcGlyGlyValNH$_2$ is given in FIG. 1, where the peptide has the designation No. 3.

EXAMPLE 5

Antagonizing effect on the stress induced intraocular pressure and pressure lowering effect in the experimentally hypertensive rabbit's eye of the dipeptide ester Glycyl-L-Valine-Benzylester, H-Gly-Val-OBzl (SEQ ID NO.9).

The peptide was applied topically as a 1% solution in 0.9% aqueous NaCl and tested in the two models as described in Examples 1 and 4.

| Antagonizing Effect | Pressure Lowering Effect |
| --- | --- |
| Active | Active |

The time curve for pressure lowering effect in the waterload model for this compound is given in FIG. 2, where the peptide has the designation No. 1.4.

EXAMPLE 6

Pressure lowering effect of a dipeptide containing the sequence βAla-Val on water load induced hypertension in the rabbit's eye by single dose treatment, the dipeptide ester β-alanyl L-valine Benzylester, H-β-Ala-Val-OBzl (SEQ ID NO.10).

50 μl of 1% solution of the peptides in 0.9% isotonic saline containing TRIS-buffer pH 7.4 was applied in one eye and 50 μl of 0.9% isotonic saline containing TRIS-buffer. pH 7.4 in the other eye 30 minutes after the interperitonal water loading and intraocular pressure was measured in both eyes for 2 hours and the difference calculated.

| Peptide | Pressure Lowering Effect |
| --- | --- |
| H-β-Ala-Val-OBzl (SEQ ID NO. 10) | Active |

The time curve for the pressure lowering effect in the waterload model for this peptide is given in FIG. 3, where the peptide has the designation No. 109.

Synthesis of compounds according to the invention

The abbreviations used in this description for amino acids and protecting groups are in agreement with the IUPAC-IUB standard rules for nomenclature.

In addition; and in particular, the following abbreviations are used:

| | | |
| --- | --- | --- |
| HONSu | : | N-hydroxysuccinimide |
| DCC | : | Dicyclohexylcarbodiimide |
| Boc | : | tert.-butyloxycarbonyl |
| OBzl | : | Benzylester |
| DMF | : | Dimethylformamide |
| DCU | : | Dicyclohexylurea |
| TEA | : | Triethylacetic acid |
| EtOAc | : | Ethylacetate |
| OEt | : | Ethylester |
| Ac | : | Acetyl |

EXAMPLE 7

Synthesis of G1]-Val-OBzl (SEQ ID NO.9)
Boc-Gly-Val-OBzl (SEQ ID NO.14)

4.4 g (25 mmoles) Boc-Gly-OH and 3.0 g (26.3 mmoles) HONSu were dissolved in 50 ml DMF and cooled to 0° C. in an icebath. 5.6 g (27.5 mmoles) DCC dissolved in 50 ml cold DMF was then added and the mixture was stirred cold for 5 hours. 10.4 g (27.5 mmoles) of Val-OBzl paratosylate were then added, dissolved in 50 ml DMF and 3.8 ml (27.5 mmoles) TEA. The mixture was stirred at room temperature overnight, and further for one day, following addition of further 2.0 ml TEA. The mixture was then filtered, evaporated to dryness and dissolved in EtOAc and extracted with aqueous NaHCO$_3$ followed by extraction with 10% citric acid, dried and again taken to dryness under reduced pressure to give an oil. Yield 10.0 g (92%).

HCl, Gly-Val-OBzl (SEQ ID NO.9)

To 9.0 g (20.6 mmoles) oily Boc-Gly-Val-OBzl (SEQ ID NO.14) were added 250 ml 2.6M HCl in EtOAc. The mixture was stirred for 80 min. and taken to dryness Under reduced pressure. Following repeated additions of EtOAc and evaporation to dryness under reduced pressure HCl, Gly-Val-OBzl (SEQ ID NO.9) was isolated as a white powder, Yield 5.6 g (79%).

EXAMPLE 8

Synthesis of Ac-Gly-Gly-Val-NH$_2$ (SEQ ID NO.8)

1.75 g (10 mmoles) Ac-Gly-Gly-OH and 1.73 g (15 mmoles) HONSu were dissolved in 25 ml acetonitrile and cooled to 0° C. 2.46 g DCC (12 mmoles) were then added, the mixture allowed to warm to room temperature and stirred for 2 hours until complete formation of the active ester. After filtering off the DCU, 1.16 g of Val-NH$_2$ free base (10 mmoles) in 25 ml H$_2$O at pH 8 were added slowly and pH maintained above 7. At completion of the reaction the acetonitrile was removed under vacuum and a small residue filtered off from the aqueous phase. The product was then purified by reverse phase HPLC using water/ethanol/acetic acid buffers.

Yield 0.8 g (34%). Purity by HPLC: >95% at 220 nm.

$^{13}$C-NMR proved correct structure by assignment of all carbon atoms.

---

We claim:
1. A peptidic compound selected from the group consisting of:

| | |
|---|---|
| H-Gly-Gly-Val-OEt | (Sequence ID No. 3), |
| H-Asn-Gly-Gly-Val-NH$_2$ | (Sequence ID No. 4), |
| Ac-Gly-Gly-Val-NH$_2$ | (Sequence ID No. 8), |
| H-Asn-Leu-Gly-Val-NH$_2$ | (Sequence ID No. 5), |
| H-Gly-Val-Tyr-NH$_2$ | (Sequence ID No. 7), | and pharmaceutically acceptable derivatives and salts thereof.

2. A pharmaceutical composition containing an effective antiglaucoma or intraocular pressure lowering amount of at least one active compound selected from the group consisting of the peptidic compounds according to claim 1, H-Gly-Val-OBzl (Sequence ID No. 9), H-β-Ala-Val-OBzl (Sequence ID No. 10) and pharmaceutically acceptable derivatives and salts thereof in a pharmaceutically acceptable diluent or excipient.

3. A pharmaceutical composition according to claim 2, wherein the amount of peptidic compound is 0.01–10 percent by weight.

4. A pharmaceutical composition according to claim 2, wherein the amount of peptidic compound is 0.1–5 percent by weight.

5. A pharmaceutical composition according to claim 2, wherein the amount of peptidic compound is 0.25–1 percent by weight.

6. A method for the treatment of glaucoma or intraocular hypertension comprising administering to a mammal an effective antiglaucoma or intraocular pressure lowering amount of at least one peptidic compound of formula I:

or an ω-amino-α-carboxy cyclic form thereof, or a compound transformed into or releasing any of the above basic structures under physiological conditions in humans, wherein R$_1$ is —H, or where R is —H, straight or branched alkyl or cycloalkyl up to C$_{20}$, optionally containing double bonds and/or substituted with halogen, nitro, amino, sulfo, phospho or carboxyl, or aralkyl or aryl optionally mono- or polysubstituted with halogen, hydroxy, nitro, amino, sulfo, phospho, carboxy or alkyl, or R or R$_1$ is glycosyl, nucleosyl, or R$_1$ is an L- or D-α amino acid, F is or absent, wherein R$_1$' is as defined for R$_1$ and is absent, when the compound is an N—C-cyclic form, a is 0, 1 or 2, C$_x$ and C$_y$ are tetrahedral carbon atoms (SP3 hybridized) independently having R or S configuration or C$_x$ is achiral, C$_z$ is a triplanar carbon atom (SP2 hybridized) and D is absent or C$_z$ is a tetrahedral carbon atom and D is H$_2$, A is —H or —CH$_3$, B is with respect to C$_y$ α- or β-branched C$_3$–C$_7$ alkyl or C$_4$–C$_7$ cycloalkyl, or phenyl or benzyl,

[P] is a peptide bond CO—NH, substituted forms thereof, e.g. CO—NR$_6$, wherein R$_6$ is C$_1$–C$_3$ alkyl, or isosteres thereof such as CH$_2$—NH, CH$_2$—S, CO—CH$_2$, retroinverse forms thereof, such as NH—CO, R$_2$ is —H, —OH, —CH$_3$, —NH—NH$_2$, —NHOH or —NR$_3$R$_4$, wherein R$_3$ and R$_4$ are independently —H, straight or branched alkyl or cycloalkyl, aralkyl or aryl optionally mono- or polysubstituted with hydroxy, halogen, carboxy, sulfo, phospho, amino or nitro, —OR$_5$, where R$_5$ is —H, straight or branched alkyl or cycloalkyl, aralkyl or aryl, optionally substituted as defined for R$_3$ and R$_4$, O-glycosyl, or an L- or D-α amino acid, or R$_2$ is absent when the compound is an N—C cyclic form, b is 1, 2, 3 or 4, and wherein hydrogen atoms may be replaced by fluorine, or a pharmaceutically acceptable salt thereof.

7. A method for the treatment of glaucoma or intraocular hypertension comprising administering to a mammal an effective antiglaucoma or intraocular pressure lowering amount of at least one peptidic compound of the general formula I' or a pharmaceutically acceptable derivative or salt thereof, wherein

C is Gly, β-Ala, Ala or GABA,

G is Val, Ile, tert.Leu, Leu, Tyr, Phe or cyclohexylalanin, in L-configuration,

[P] is a peptide bond CO—NH, substituted forms thereof, e.g. CO—NR$_6$, wherein R$_6$ is C$_1$–C$_3$ alkyl, or isosteres thereof such as CH$_2$—NH, CH$_2$—S, CO—CH$_2$, retroinverse forms thereof, such as NH—CO, b is 1, 2, 3, or 4, R$_1$ is —H, or where R is —H, straight or branched alkyl or cycloalkyl up to C$_{20}$, optionally containing double bonds and/or substituted with halogen, nitro, amino, sulfo, phospho or carboxyl, or aralkyl or aryl optionally mono- or polysubstituted with halogen, hydroxy, nitro, amino, sulfo, phospho, carboxy or alkyl, or R or R$_1$ is glycosyl, nucleosyl, or R$_1$ is an L- or D-α amino acid, and R$_2$ is —H, —OH, —CH$_3$, —NH—NH$_2$, —NHOH, —NR$_3$R$_4$, wherein R$_3$ and R$_4$ are independently —H, straight or branched alkyl or cycloalkyl, aralkyl or aryl optionally mono- or polysubstituted with hydroxy, halogen, carboxy, sulfo, phospho, amino or nitro, —OR$_5$, where R$_5$ is —H, straight or branched alkyl or cycloalkyl, aralkyl or aryl, optionally substituted as defined for $R_3$ and $R_4$, O-glycosyl, or an L- or D-α amino acid, or $R_2$ is absent when the compound is an N—C cyclic form.

8. A method according to claim 7 comprising administering to a mammal an effective antiglaucoma or intraocular pressure lowering amount of at least one peptidic compound of the general formula I' containing the sequence C'-Val wherein C' is β-Ala or Gly or a pharmaceutically acceptable derivative or salt thereof.

9. A method for the treatment of glaucoma or intraocular hypertension comprising administering to a mammal an effective antiglaucoma or intraocular pressure lowering amount of at least one compound selected from the group consisting of:

| | |
|---|---|
| H-Gly-Gly-Val-OEt | (Sequence ID No. 3), |
| H-Asn-Gly-Gly-Val-NH₂ | (Sequence ID No. 4), |
| H-Asn-Leu-Gly-Val-NH₂ | (Sequence ID No. 5), |
| H-Asn-Leu-Gly-Tyr-NH₂ | (Sequence ID No. 6), |
| H-Gly-Val-Tyr-NH₂ | (Sequence ID No. 7), |
| Ac-Gly-Gly-Val-NH₂ | (Sequence ID No. 8), |
| H-Gly-Val-OBzl | (Sequence ID No. 9), |
| H-β-Ala-Val-OBzl | (Sequence ID No. 10) | and pharmaceutically acceptable derivatives and salts thereof.

* * * * *